(12) United States Patent
Kavoori Sethumadhavan et al.

(10) Patent No.: US 9,645,076 B2
(45) Date of Patent: May 9, 2017

(54) SYSTEMS AND METHODS TO ANALYZE A GAS-MIXTURE

(71) Applicant: General Electric Company, Schenectady, NY (US)

(72) Inventors: Nagapriya Kavoori Sethumadhavan, Bangalore (IN); Sandip Maity, Bangalore (IN); Samhitha Palanganda Poonacha, Bangalore (IN); Moitrayee Mukherjee, Bangalore (IN); Purbasha Halder, Bangalore (IN); Harish Sasikumar, Bangalore (IN); Prasenjit Pandey, Kolkata (IN)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 14/583,288

(22) Filed: Dec. 26, 2014

(65) Prior Publication Data
US 2016/0187251 A1    Jun. 30, 2016

(51) Int. Cl.
*G01N 21/25* (2006.01)
*G01N 21/31* (2006.01)
(Continued)

(52) U.S. Cl.
CPC ............. *G01N 21/31* (2013.01); *G01J 3/433* (2013.01); *G01N 21/03* (2013.01); *G01N 21/39* (2013.01);
(Continued)

(58) Field of Classification Search
CPC ............ G01J 3/42; G01N 21/59; G01N 21/27
See application file for complete search history.

(56) References Cited

U.S. PATENT DOCUMENTS

| | | | |
|---|---|---|---|
| 5,640,245 A | 6/1997 | Zybin et al. | |
| 5,973,782 A | 10/1999 | Bomse | |

(Continued)

FOREIGN PATENT DOCUMENTS

| | | |
|---|---|---|
| JP | 2011153980 A | 8/2011 |
| WO | 2013096396 A1 | 6/2013 |

OTHER PUBLICATIONS

Rieker et al., "Calibration-free wavelength-modulation spectroscopy for measurements of gas temperature and concentration in harsh environments", Applied Optics, Optics Info Base, vol. 48, Issue: 29, pp. 5546-5560, 2009.

(Continued)

*Primary Examiner* — Tarifur Chowdhury
*Assistant Examiner* — Jamil Ahmed
(74) *Attorney, Agent, or Firm* — Nitin N. Joshi (57) ABSTRACT

A method for determining a concentration of at least one individual gas present in a gas-mixture includes irradiating a first component by incident modulated-light-beams characterized by a determined absorption wavelength range, modulation frequencies and a modulation amplitudes to generate first transmitted-light-beams, irradiating a second component, comprising a determined concentration of the at least one individual gas, by the first incident modulated-light-beams to generate second transmitted-light-beams, generating noise signals representative of a characteristic of the first transmitted-light-beams, generating noise-free signals representative of a characteristic of the second transmitted-light-beams, selecting an optimal modulation frequency and an optimal modulation amplitude from the modulation frequencies and the modulation amplitudes based on the noise signals and the noise-free signals, and determining a concentration of the at least one individual gas in the gas-mixture based on the optimal modulation fre- (Continued)

quency and the optimal modulation amplitude of the determined absorption wavelength range.

11 Claims, 6 Drawing Sheets

(51) Int. Cl.
  *G01J 3/433* (2006.01)
  *G01N 21/39* (2006.01)
  *G01N 21/03* (2006.01)
  *G01N 21/3504* (2014.01)

(52) U.S. Cl.
  CPC ... *G01N 21/3504* (2013.01); *G01N 2201/061* (2013.01)

(56) References Cited

U.S. PATENT DOCUMENTS

| | | |
|---|---|---|
| 6,356,350 B1 | 3/2002 | Silver et al. |
| 6,940,599 B1 | 9/2005 | Hovde |
| 7,230,711 B1 | 6/2007 | Hovde |
| 7,969,576 B1 | 6/2011 | Buckley et al. |
| 8,395,777 B2 | 3/2013 | Rao |
| 2011/0150035 A1 | 6/2011 | Hanson et al. |
| 2012/0252137 A1 | 10/2012 | Novitsky et al. |
| 2013/0163000 A1* | 6/2013 | Ido ............... G01N 21/59 356/437 |
| 2014/0036954 A1 | 2/2014 | Maity et al. |
| 2014/0049777 A1* | 2/2014 | Sun ............... G01J 3/42 356/409 |
| 2014/0253922 A1* | 9/2014 | Liu ............... G01N 21/274 356/437 |
| 2015/0153883 A1 | 6/2015 | Goo et al. |

OTHER PUBLICATIONS

Cao et al., "Etalon Effects Analysis in Tunable Diode Laser Absorption Spectroscopy Gas Concentration Detection System Based on Wavelength Modulation Spectroscopy", Photonics and Optoelectronic (SOPO), 2010 Symposium on, IEEE Xplore, pp. 1-5, Jun. 19-21, 2010, China.

Reid J., et al., "Sensitivity Limits of a Tunable Diode Laser Spectrometer with Application to the Detection of No2 at 100-ppt Level", Applied Optics, vol. 19 (19), pp. 3349-3354, 1980.

Kluczynski P., et al., "Background Signals in Wavelength-Modulation Spectrometry by Use of Frequency-Doubled Diode-Laser Light II Experiment", Applied Optics, vol. 40 (6), pp. 794-805, 2001.

Maw., et al., "High-Sensitivity Detection of Methane Near 6106 cm-1 Using Tunable External-Cavity Diode Laser", Japanese Journal of Applied Physics, vol. 44 (4A), pp. 1961-1965, 2005.

Mihail B., et al., "Multiplexed gas spectroscopy using tunable VCSELs", Advanced Environmental, Chemical, And Biological Sensing Technologies IX, Proceeding of SPIE, vol. 8366 (1), pp. 1-6, 2012.

Neethu S., et al., "Validation of Wavelength Modulation Spectroscopy Techniques for Oxygen Concentration Measurement", Sensors and Actuators B: Chemical International Journal Devoted to Research and Development of Physical and Chemical Transducers, vol. 192, pp. 70-76, 2013.

European Search Report Issued in Connection with Corresponding EP Application No. 15200356.2 on Jun. 3, 2016.

* cited by examiner

SYSTEMS AND METHODS TO ANALYZE A GAS-MIXTURE

BACKGROUND

Electrical equipment such as transformers use fluids such as castor oil, mineral oil and synthetic oils for insulation purposes. The parameters of the fluid are indicative of incipient faults in the electrical equipment. The parameters of the fluid among other things include information about the concentration of dissolved gases. Examples of dissolved gases include carbon monoxide, carbon dioxide, hydrocarbons, oxygen and nitrogen. Specifically, carbon monoxide and carbon dioxide increase in concentration with thermal aging and degradation of insulation of the electrical equipment. Furthermore, hydrocarbons such as acetylene and ethylene increase in concentration due to dielectric breakdown caused by corona and arcing. Further, concentrations of oxygen and nitrogen are indicative of condition of a gas pressurizing system of the equipment. Accordingly, the dissolved gases may be extracted from equipment (such as transformers) and analyzed to determine incipient faults in the equipment.

Typically, absorption spectroscopy technique may be used for analyzing a gas-mixture. For increased sensitivity, wavelength modulation absorption spectroscopy technique may be used to analyze a gas-mixture. The wavelength modulation absorption spectroscopy technique, for example, employs irradiation of a gas-mixture by a scanned modulated-light-beam (hereinafter "incident modulated-light-beam") resulting in absorption of a portion of the incident modulated-light-beam by gases present in the gas-mixture, and transmission of rest (hereinafter referred to as "transmitted-light-beam") of the incident modulated-light-beam from the gas-mixture. Due to absorption of the portion of the incident modulated-light-beam, the intensity of the transmitted-light-beam is less than the incident modulated-light-beam at an absorption peak of an individual gas present in the gas-mixture. A detector detects the transmitted-light-beam to generate a signal representative of intensity of the transmitted-light-beam as a function of wavelength. For example, the Beer Lambert law may be used to measure concentrations of the gases present in the gas-mixture based on an amount of absorption of the incident modulated-light-beam by the gases. The amount of absorption of the incident modulated-light-beam, for example, may be determined based on the intensity of the incident modulated-light-beam and the signal representative of the intensity of the transmitted-light-beam. The gas concentration, for example, may also be determined using the amplitude of the intensity signal at the second harmonic of the modulation frequency.

Typically, the incident modulated-light-beam characterized by a modulation frequency of if and a modulation amplitude of 2.2 times half-width half-maximum (HWHM) of the absorption peak is used in wavelength modulation absorption spectroscopy techniques. Typically the modulation amplitude of 2.2 times half-width half-maximum (HWHM) of the absorption peak is believed to result in generation of an optimal 2 f signal. The modulation frequency generally used is much larger than the scan frequency with no other special criterion. However, usage of the 2.2 times HWHM modulation amplitude and any modulation frequency may result in high noise (for example etalon noise and electronic noise) in the signal representative of the intensity of the transmitted-light-beam resulting in low signal-to-noise ratio. The low signal-to-noise ratio may lead to inaccurate analysis of the gas-mixture. For example, the low signal to noise ratio may result in inaccurate determination of the concentrations of the gases present in the gas-mixture.

Accordingly, it is desirable to provide systems and methods that may provide accurate measurements of gases present in a gas-mixture. Particularly, it is desirable to provide systems and methods that may determine optimal modulation frequency and optimal modulation amplitude for different wavelengths of an incident modulated-light-beam to increase the signal-to-noise ratio resulting in accurate measurements of gases present in a gas-mixture.

BRIEF DESCRIPTION

In accordance with one embodiment, a method for determining a concentration of at least one individual gas present in a gas-mixture is presented. The method includes irradiating a first component, comprising substantially zero concentration of the at least one individual gas, by a plurality of first incident modulated-light-beams characterized by a determined absorption wavelength range, a plurality of modulation frequencies and a plurality of modulation amplitudes to generate a plurality of first transmitted-light-beams, irradiating a second component, comprising a determined concentration of the at least one individual gas, by the plurality of first incident modulated-light-beams to generate a plurality of second transmitted-light-beams, generating a plurality of noise signals representative of a characteristic of the plurality of first transmitted-light-beams, generating a plurality of noise-free signals representative of a characteristic of the plurality of second transmitted-light-beams, selecting an optimal modulation frequency and an optimal modulation amplitude from the plurality of modulation frequencies and the plurality of modulation amplitudes based on the plurality of noise signals and the plurality of noise-free signals, and determining a concentration of the at least one individual gas in the gas-mixture based on the optimal modulation frequency and the optimal modulation amplitude of the determined absorption wavelength range, wherein the determined absorption wavelength range corresponds to the at least one individual gas in the gas-mixture.

In accordance with another embodiment, a system for determining a concentration of at least one individual gas present in a gas-mixture is presented. The system includes a first tunable radiation source that generates and directs a plurality of first incident modulated-light-beams to irradiate a first component, comprising substantially zero concentration of the at least one individual gas, to generate a plurality of first transmitted-light-beams, wherein the plurality of first incident modulated-light-beams are characterized by a determined absorption wavelength range, a plurality of modulation frequencies and a plurality of modulation amplitudes, generates and directs the plurality of first incident modulated-light-beams to irradiate a second component comprising a determined concentration of the at least one individual gas to generate a plurality of second transmitted-light-beams, a first detector that generates a plurality of noise signals based on the plurality of first transmitted-light-beams, and a plurality of noise-free signals based on the plurality of second transmitted-light-beams, a processing subsystem that selects an optimal modulation frequency and an optimal modulation amplitude from the plurality of modulation frequencies and the plurality of modulation amplitudes based on the plurality of noise signals and the plurality of noise-free signals, a subsystem that determines a concentration of the at least one individual gas in the gas-mixture based on the optimal modulation frequency and the optimal modulation amplitude of the determined absorption wavelength range, wherein the determined absorption wavelength range corresponds to the at least one individual gas in the gas-mixture.

In accordance with still another embodiment, a method for analyzing a gas-mixture is presented. The method includes irradiating a gas-mixture by a plurality of first incident modulated-light-beams, characterized by a determined absorption wavelength range, a plurality of modulation frequencies and a plurality of modulation amplitudes, to generate a plurality of first transmitted-light-beams, wherein at least one individual gas in the gas-mixture substantially absorbs photons of the plurality of first incident modulated-light-beams, generating a plurality of response signals based on the plurality of first transmitted-light-beams, selecting an optimal modulation frequency and an optimal modulation amplitude from the plurality of modulation frequencies and the plurality of modulation amplitudes based on the plurality of response signals, and determining a concentration of the at least one individual gas in the gas-mixture at least based on the optimal modulation frequency and the optimal modulation amplitude.

A system for determining a concentration of at least one individual gas present in a gas-mixture is presented. The system includes a first radiation source that irradiates a gas-mixture by a plurality of first incident modulated-light-beams, characterized by a determined absorption wavelength range, a plurality of modulation frequencies and a plurality of modulation amplitudes, to generate a plurality of first transmitted-light-beams, wherein the at least one individual gas present in the gas-mixture substantially absorbs photons of the plurality of first incident modulated-light-beams, a detector that generates a plurality of response signals based on the plurality of first transmitted-light-beams, a processing subsystem that selects an optimal modulation frequency and an optimal modulation amplitude from the plurality of modulation frequencies and the plurality of modulation amplitudes based on a plurality of signal-to-noise ratios of the plurality of response signals, and a subsystem that determines a concentration of the at least one individual gas in the gas-mixture based on the determined absorption wavelength range, the optimal modulation frequency and the optimal modulation amplitude.

DRAWINGS

These and other features and aspects of embodiments of the present systems and methods will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this disclosure belongs. The terms "a" and "an" do not denote a limitation of quantity, but rather denote the presence of at least one of the referenced items. The term "or" is meant to be inclusive and mean one, some, or all of the listed items. The use of "including," "comprising" or "having" and variations thereof herein are meant to encompass the items listed thereafter and equivalents thereof as well as additional items. The terms "processing subsystem", "control system" or "controller" may include either a single first component or a plurality of first components, which are either active and/or passive and are connected or otherwise coupled together to provide the described function or functions. The term "processing subsystem" may include a digital signal processor, a microprocessor, a microcomputer, a microcontroller, and/or any other suitable device.

Figure 1:
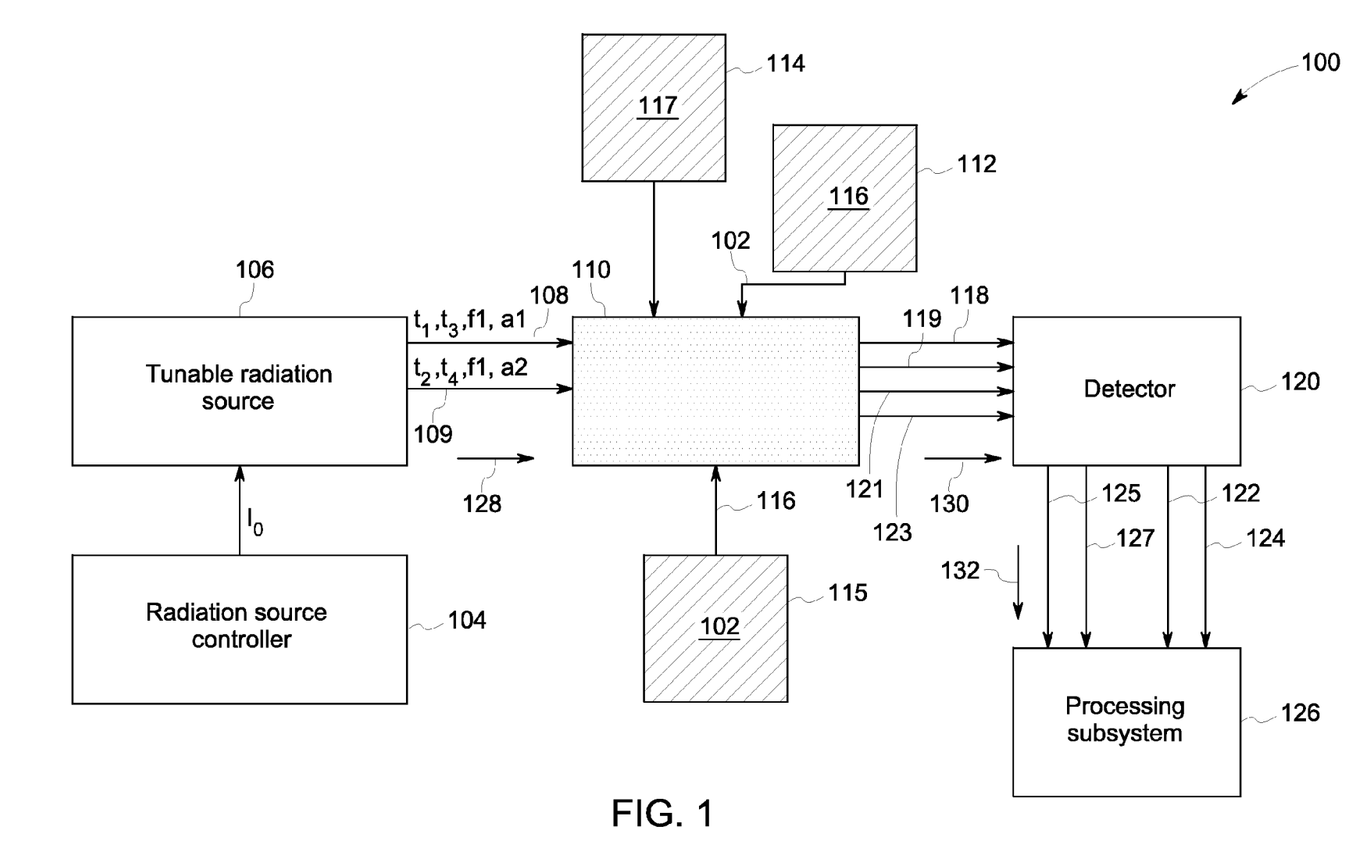
FIG. 1 shows an example of a gas-analyzer system that uses a wavelength modulation absorption spectroscopy technique to determine one or more optimal modulation frequencies and optimal modulation amplitudes for analysis of a gas-mixture, in accordance with certain embodiments of the present techniques.

FIG. 1 shows an example of a gas-analyzer system 100 that uses a wavelength modulation absorption spectroscopy technique to determine one or more optimal modulation frequencies and optimal modulation amplitudes for analysis of a gas-mixture 102, in accordance with certain embodiments of the present techniques. In one embodiment, the present systems and techniques determine an optimal modulation frequency and an optimal modulation amplitude of a determined absorption wavelength range of each individual gas present in the gas-mixture 102. The gas-mixture 102, for example may be a mixture of dissolved gases including carbon monoxide, carbon dioxide, hydrocarbons, oxygen and nitrogen For ease of understanding, the following description explains analysis of an individual gas $G_1$ present in the gas-mixture 102. The individual gas $G_1$ corresponds to a determined absorption wavelength range $G_{w1}$. In other words, if the individual gas $G_1$ is irradiated by an incident modulated-light-beam characterized by the determined absorption wavelength range $G_{w1}$, then the individual gas $G_{w1}$ absorbs at least a portion of photons of the incident modulated-light-beam. It is noted that the determined absorption wavelength range $G_{w1}$ of the individual gas $G_1$ may change with variations in temperature and pressure of the individual gas $G_1$.

The system 100 includes a radiation source controller 104 and a tunable radiation source 106, wherein the radiation source controller 104 is configured to control the tunable radiation source 106 to generate first incident modulated-light-beam characterized by the determined absorption wavelength range $G_{w1}$, a plurality of modulation frequencies and a plurality of modulation amplitudes. Particularly, the radiation source controller 104 supplies an injection current $I_0$ to the tunable radiation source 106 to generate the first incident modulated-light-beam characterized by the determined absorption wavelength range $G_{w1}$, a plurality of modulation frequencies and a plurality of modulation amplitudes. Accordingly, the radiation source controller 104 may adjust the injection current $I_0$ to change the modulation frequencies and the modulation amplitudes of the first incident modulated-light-beam. It is noted that the system 100 may further include a lock-in amplifier (not shown), a function generator (not shown) and a mixer (not shown) to generate the incident modulated-light-beam. The tunable radiation source 106, for example, may be a coherent source, an incoherent source, a visible light source, an infrared source, or the like. The coherent source, for example, is a tunable diode laser, a quantum cascade laser, a laser, or the like. The incoherent source may be a Light Emitting Diode (LED).

The system 100 further includes an absorption cell 110, a first filling-chamber 112, a second filling-chamber 114 and a third filling chamber 115. The first filling-chamber 112 contains a first component 116, the second filling-chamber 114 contains a second component 117, and the third filling-chamber 115 contains the gas-mixture 102. The first component 116 is selected from a gas, a fluid, or a gas-mixture such that when the first component 116 is irradiated by the first incident modulated-light-beam characterized by the determined absorption wavelength range $G_{w1}$, the first component 116 fails to absorb photons of the first incident modulated-light-beam characterized by the determined absorption wavelength range $G_{w1}$ due to inherent properties of the first component 116. The first component 116 is selected from a gas, a fluid, or a gas-mixture such that the first component 116 contains minimal or substantially zero amount of the individual gas $G_1$ which would result in non-absorption of the incident modulated-light-beam characterized by the determined absorption wavelength range corresponding to the individual gas $G_1$.

For determining the optimal modulation frequency and the optimal modulation amplitude of the determined absorption wavelength range $G_{w1}$ of the individual gas $G_1$ present in the gas-mixture 102, the absorption cell 110 is filled with the first component 116 from the first filling-chamber 112. In one embodiment, vacuum may be created inside the absorption cell 110 rather than filling the first component 116 in the absorption cell 110. The absorption cell 110 is filled with the first component 116 at a determined temperature and a determined pressure. While in the presently contemplated configuration, the absorption cell 110 is filled with the first component 116, in an alternative embodiment vacuum may be created inside the absorption cell 110. After filling the absorption cell 110 with the first component 116, the radiation source controller 104 controls the tunable radiation source 106 to generate the first incident modulated-light-beam characterized by the determined absorption wavelength range $G_{w1}$ at a plurality of modulation frequencies and a plurality of modulation amplitudes for a time period. In other words, at different time stamps the first incident modulated-light-beam is characterized by the determined absorption wavelength range $G_{w1}$, a different modulation frequency and/or different modulation amplitude. The first incident modulated-light-beam is directed into the absorption cell 110 to irradiate the first component 116.

At a time stamp $t_1$, the tunable radiation source 106 generates a first incident modulated-light-beam 108 characterized by the determined absorption wavelength range $G_{w1}$, a first modulation frequency f1, and a first modulation amplitude a1 to irradiate the first component 116. Furthermore, at a second time stamp $t_2$, the tunable radiation source 106 generates a first incident modulated-light-beam 109 characterized by the determined absorption wavelength range $G_{w1}$, the first modulation frequency f1 and a second modulation amplitude a2 to irradiate the first component 116. For ease of understanding, FIG. 1 shows irradiation of the first component 116 by the two first incident modulated-light-beams 108, 109 at the times stamps $t_1$, $t_2$, respectively, however the first component 116 may be irradiated by multiple first incident modulated-light-beams characterized by the determined absorption wavelength range $G_{w1}$ and multiple different modulation frequencies and modulation amplitudes at multiple time stamps.

The direction of the first incident modulated-light-beams 108, 109 into the absorption cell 110 irradiates the first component 116 filled in the absorption cell 110. Due to inherent properties of the first component 116 or substantial absence of the individual gas $G_1$ in the first component 116, the first component 116 substantially fails to absorb the photons of the first incident modulated-light-beams 108, 109. As used herein, the phrase "substantially fails to absorb" is used to refer to fractional absorbance below about $1e^{-5}$. Though the first component 116 substantially fails to absorb the photons of the first incident modulated-light-beams 108, 109; still a characteristic of the first incident modulated-light-beams 108, 109 changes due to one or more of phenomena, such as, electronic noise, etalon noise etc. The characteristic of the first modulated-light-beam 108, 109, for example may include energy, intensity, or the like. For example, etalon noise and/or the electronic noise in the system 100 change an intensity and/or energy of the first incident modulated-light-beams 108, 109. Hereinafter, the first incident modulated-light-beams 108, 109 transmitting out of the absorption cell 110 with at least one changed characteristic is referred to as "first transmitted-light-beam/s."

The irradiation of the first component 116 by the first incident modulated-light-beams characterized by the determined absorption wavelength range $G_{w1}$ with varying modulation frequencies and varying modulation amplitudes for the time period changes the characteristic of the first incident modulated-light-beams 108, 109 due to one or more phenomena resulting in generation of multiple first transmitted-light-beams. The irradiation of the first component 116 by the first incident modulated-light-beam 108, at the time stamp $t_1$, characterized by the determined absorption wavelength range $G_{w1}$, the first modulation frequency f1 and the first modulation amplitude a1 results in generation of a first transmitted-light-beam 118. Similarly, the irradiation of the first component 116 by the first incident modulated-light-beam 109, at the second time stamp $t_2$, characterized by the determined absorption wavelength range $G_{w1}$, the first modulation frequency f1 and the second modulation amplitude a2 results in generation of a first transmitted-light-beam 119.

The system 100 further comprises a detector 120 operationally coupled to the absorption cell 110. In the presently contemplated configuration, the detector 120 receives the first transmitted-light-beams 118, 119 from the absorption cell 110. The detector 120 generates a noise signal 122 based on a characteristic of the first transmitted-light-beam 118, and a noise signal 124 based on a characteristic of the first transmitted-light-beam 119. The noise signals 122, 124, for example, may include second harmonic signals. The characteristic of the first transmitted-light-beams 118, 119, for example may include an intensity and/or energy of the first transmitted-light-beams 118, 119.

Subsequent to the generation of the noise signals 122, 124, the absorption cell 110 is emptied of the first component 116, and the second component 117 is filled into the absorption cell 110 from the second filling-chamber 114. It is noted that the second component 117 is selected by a user such that at least one of the following (a) to (c) conditions are satisfied:

a.) The second component 117 contains high concentration of the individual gas $G_1$.

b.) When the second component 117 is irradiated by an incident modulated-light-beam characterized by the determined absorption wavelength range $G_{w1}$, the second component 117 substantially absorbs photons of the incident modulated-light-beam due to inherent properties and high concentration of the individual gas $G_1$ in the second component 117.

c.) The second component 117 is selected such that a signal-to-noise ratio of signals generated using absorption spectroscopy technique on the second component 117 is at least 10.

After filling the absorption cell 110 with the second component 117, the tunable radiation source 106 again generates the first incident modulated-light-beams characterized by the determined absorption wavelength range $G_{w1}$ with the plurality of modulation frequencies and the plurality of modulation amplitudes for a time period to irradiate the second component 117. At a time stamp $t_3$, the tunable radiation source 106 generates the first incident modulated-light-beam 108 characterized by the determined absorption wavelength range $G_{w1}$, the first modulation frequency f1, and the first modulation amplitude a1 to irradiate the second component 117. Furthermore, at a time stamp $t_4$, the tunable radiation source 106 generates the first incident modulated-light-beam 109 characterized by the determined absorption wavelength range $G_{w1}$, the first modulation frequency f1 and a second modulation amplitude a2 to irradiate the second component 117. For ease of understanding, FIG. 1 shows irradiation of the second component 117 by the two first incident modulated-light-beams 108, 109 at the times stamps $t_3$, $t_4$, respectively, however the second component 117 may be irradiated by multiple first incident modulated-light-beams characterized by the determined absorption wavelength range $G_{w1}$ and multiple different modulation frequencies and modulation amplitudes at multiple time stamps.

The direction of the first incident modulated-light-beams 108, 109 into the absorption cell 110 irradiates the second component 117 filled in the absorption cell 110. The irradiation of the second component 117 by the first incident modulated-light-beams characterized by the determined absorption wavelength range $G_{w1}$ with varying modulation frequencies and varying modulation amplitudes for the time period results in absorption of the photons of the first incident modulated-light-beams 108, 109 by the individual gas $G_1$ present in the gas-mixture 102 resulting in generation of multiple second transmitted-light-beams. In the presently contemplated configuration, the irradiation of the second component 117 by the first incident modulated-light-beam 108, at the time stamp $t_3$ results in generation of a second transmitted-light-beam 121. Similarly, the irradiation of the second component 117 by the first incident modulated-light-beam 109, at the time stamp $t_4$ results in generation of a second transmitted-light-beam 123.

The detector 120 receives the second transmitted-light-beams 121, 123 from the absorption cell 110. In the presently contemplated configuration, the detector 120 generates a noise-free signal 125 based on a characteristic of the second transmitted-light-beam 121, and a noise-free signal 127 based on a characteristic of the second transmitted-light-beam 123. The characteristic of the second transmitted-light-beams 121, 123, for example may include an intensity and/or energy of the second transmitted-light-beams 121, 123. The noise-free signals 125, 127, for example, may include second harmonic signals. The noise-free signal 125, 127 includes substantially minimum noise, such that a signal-to-noise ratio of the noise-free signals 125, 127 is at least 10.

Furthermore, the system 100 includes a processing subsystem 126 that receives the noise signals 122, 124 from and the noise-free signals 125, 127 from the detector 120. The processing subsystem 126 selects an optimal modulation frequency and an optimal modulation amplitude from the multiple modulation frequencies and the multiple modulation amplitudes based on the noise signals 122, 124 and the noise-free signals 125, 127. In one embodiment, the processing subsystem 126 determines a plurality of signal-to-noise ratios (not shown) based on the noise-free signals 125, 127 and the noise signals 122, 124, selects the optimal modulation frequency and the optimal modulation amplitude that corresponds to maximum or a substantially high signal-to-noise ratio in the signal-to-noise ratios. A signal-to-noise ratio may be substantially high when the signal-to-noise ratio is 10. For example, the processing subsystem 126 may determine the signal-to-noise ratios by dividing an amplitude of the noise-free signals 125, 127 by an amplitude of the noise-signals 122, 124. Determination of signal-to-noise ratios is shown with reference to FIG. 5.

Subsequent to determination of the optimal modulation frequency and the optimal modulation amplitude, the gas-mixture 102 comprising the individual gas $G_1$ is filled into the absorption cell 110 from the third filling-chamber 115. Subsequent to filling the absorption cell 110 with the gas-mixture 102, the tunable radiation source 106 irradiates a second incident modulated-light-beam 128 characterized by the determined absorption wavelength range $G_{w1}$, the optimal modulation frequency and the optimal modulation amplitude. The irradiation of the second incident modulated-light-beam 128 results in absorption of photons of the second incident modulated-light-beam 128 by the individual gas $G_1$ present in the gas-mixture 102 resulting in generation of a third transmitted-light-beam 130. The detector 120 receives the third transmitted-light-beam 130 from the absorption cell 110. Subsequently, the detector 120 generates a response signal 132 based on a characteristic of the third transmitted-light-beam 130. The characteristic of the response signal 132, for example, may include an intensity and/or energy of the third transmitted-light-beam 130. For example, the response signal 132 is representative of the intensity of the third transmitted-light-beam 130.

Furthermore, the processing subsystem 126 receives the response signal 132, and determines a concentration of the individual gas $G_1$ at least based on the response signal 132. For example, the processing subsystem 126 may determine the concentration of the individual gas $G_1$ by applying a Beer-Lambert law on the response signal 132 representative of the intensity of the third transmitted-light-beam 130 and the intensity of the second incident-light-beam 128. In another embodiment, the processing subsystem 126 may determine the concentration of the individual gas $G_1$ by using a calibration plot, function or table (not shown) that maps the response signal 132 to the concentration of the individual gas $G_1$.

Figure 2A:
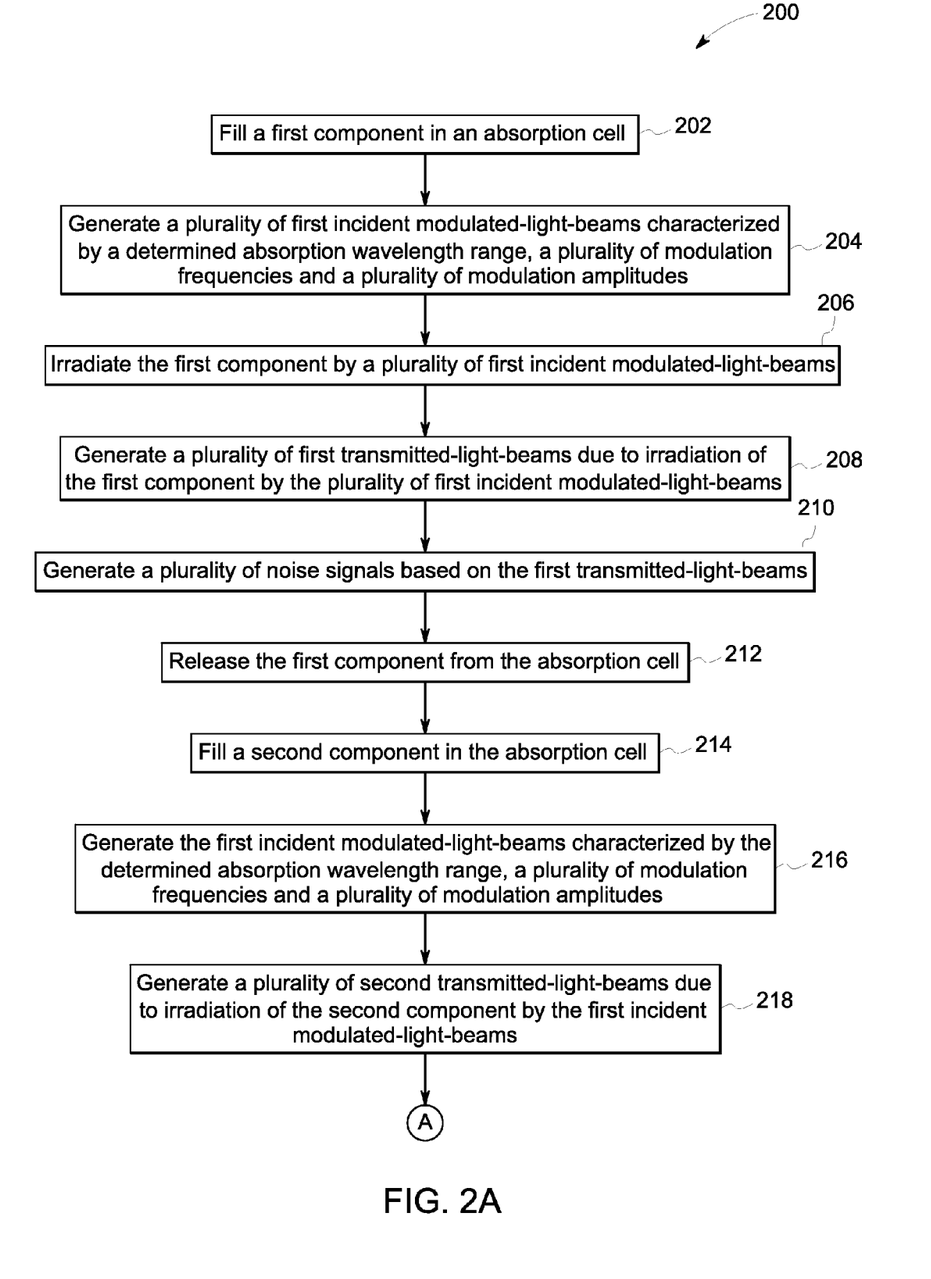
FIG. 2A and FIG. 2B is a flow chart illustrating a method for analyzing a gas-mixture comprising at least one individual gas $G_1$, in accordance with one embodiment of the present techniques.
Figure 2B:
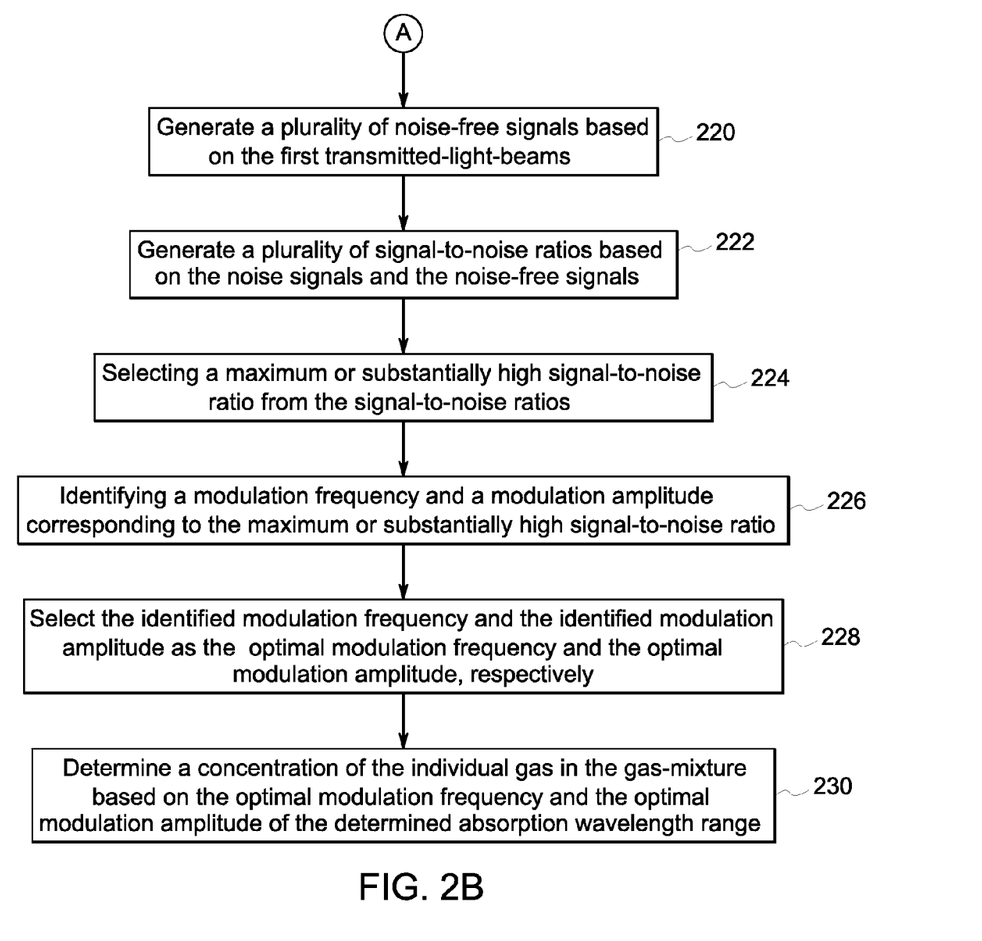

FIG. 2A and FIG. 2B is a flow chart illustrating a method 200 for analyzing a gas-mixture comprising at least one individual gas $G_1$, in accordance with one embodiment of the present techniques. The gas-mixture, for example, may be natural gas, liquid nitrogen gas, synthetic gas, liquid petroleum gas, process gas, sour gas, sweet gas, dissolved gas in transformer oil, or the like. The individual gas $G_1$ corresponds to a determined absorption wavelength range $G_{w1}$ In other words, if the individual gas $G_1$ is irradiated by an incident modulated-light-beam characterized by the determined absorption wavelength range $G_{w1}$, then the individual gas $G_{w1}$ absorbs at least a portion of photons of the incident modulated-light-beam.

At block 202, an absorption cell is filled with the first component 116 referred to in FIG. 1 or a vacuum is created inside the absorption cell 110. At block 204, the tunable radiation source 106 is controlled to generate a plurality of first incident modulated-light-beams characterized by the determined absorption wavelength range $G_{w1}$, a plurality of modulation frequencies and a plurality of modulation amplitudes. It is noted that the tunable radiation source generates the first incident modulated-light-beams characterized by the determined absorption wavelength range $G_{w1}$ that correspond to the individual gas $G_1$. For example, at a time stamp $t_1$, the tunable radiation source 106 may generate a first incident modulated-light-beam $b_1$ characterized by the determined absorption wavelength range $G_{w1}$, a first modulation frequency f1 and a first modulation amplitude a1. Similarly, at a time stamp $t_2$, the tunable radiation source 106 may generate another first incident modulated-light-beam $b_2$ characterized by a second modulation frequency f2 and a second modulation amplitude a2.

At block 206, the first incident modulated-light-beams are directed into the first component 116 to irradiate the first component 116 (or vacuum when vacuum is filled in the absorption cell 110) by the first incident modulated-light-beams. Subsequently at block 208, the irradiation of the first component 116 by the first incident modulated-light-beams characterized by the determined absorption wavelength range $G_{w1}$ changes the characteristic of the first incident modulated-light-beams due to one or more phenomena resulting in generation of multiple first transmitted-light-beams. The phenomena, for example, include etalon noise generation, electronic noise generation, or the like. For example, the irradiation of the first component 116 by the first incident modulated-light-beam $b_1$ at the time stamp $t_1$ may result in generation of a first transmitted-light-beam $TB_1$. Similarly, the irradiation of the first component 116 by the first incident modulated-light-beam $b_2$ at the time stamp $t_2$ may result in generation of a first transmitted-light-beam $TB_2$.

At block 210, a plurality of noise signals may be generated based on the first transmitted-light-beams. For example, a noise signal $N_1$ may be generated based on the first transmitted-light-beam $TB_1$. Similarly, another noise signal $N_2$ may be generated based on the first transmitted-light-beam $TB_2$. The noise signals $N_1$ and $N_2$ may be second harmonic signals (the amplitude of intensity at the second harmonic of the modulation frequencies) of the first transmitted-light-beams $TB_1$, $TB_2$. For example, the noise signals may be generated based on a characteristic of the first transmitted-light-beams. The characteristic of the first transmitted-light-beams, for example, may include an intensity or energy of the first transmitted-light-beams. The noise signals, for example, may be generated by the detector 120 referred to in FIG. 1.

Furthermore, at block 212, the first component 116 is released out from the absorption cell 110. Subsequently, at block 214, the absorption cell 110 is filled with the second component 117 referred to in FIG. 1. At block 216, the first incident modulated-light-beams characterized by the determined absorption wavelength range $G_{w1}$, the modulation frequencies and the modulation amplitudes are directed into the absorption cell 110 to irradiate the second component 117. For example, at a time stamp $t_3$, the tunable radiation source 106 may generate a first incident modulated-light-beam $b_1$ characterized by the determined absorption wavelength range $G_{w1}$, a first modulation frequency f1 and a first modulation amplitude a1. Similarly, at a time stamp $t_4$, the tunable radiation source 106 may generate another first incident modulated-light-beam $b_2$ characterized by a second modulation frequency f2 and a second modulation amplitude a2.

At block 218, the irradiation of the second component 117 by the first incident modulated-light-beams characterized by the determined absorption wavelength range $G_{w1}$ with varying modulation frequencies and varying modulation amplitudes for the time period results in absorption of the photons of the first incident modulated-light-beams by the individual gas $G_1$ present in the gas-mixture 102 resulting in generation of multiple second transmitted-light-beams. Subsequently at block 220, a plurality of noise-free signals may be generated based on the second transmitted-light-beams. For example, a noise-free signal $NF_1$ may be generated based on the second transmitted-light-beam $TB_2$. Similarly, another noise-free signal $NF_2$ may be generated based on the second transmitted-light-beam $TB_2$. For example, the noise-free signals may be generated based on a characteristic of the second transmitted-light-beams. The noise-free signals 125, 127, for example, may include second harmonic signals. The characteristic of the second transmitted-light-beams, for example, may include an intensity or energy of the first transmitted-light-beams. The characteristic of the second transmitted light beam may include the amplitude of the second harmonic signal (the amplitude of intensity at the second harmonic of the modulation frequency) of the second transmitted-light-beams. The noise-free signals, for example, may be generated by the detector 120 referred to in FIG. 1.

Subsequently, the optimal modulation frequency and the optimal modulation amplitude may be determined based on the noise signals and the noise-free signals. Determination of the optimal modulation frequency and the optimal modulation amplitude, in accordance with an example is explained in subsequent blocks 222-228. At block 222, a plurality of signal-to-noise ratios may be generated based on the noise signals generated at block 210 and the noise-free-signals generated at block 220. The signal-to-noise ratios, for example are generated by dividing the amplitude of the noise-free-signals by corresponding amplitude of the noise signals. Subsequently at block 224 a maximum signal-to-noise ratio may be selected from the multiple signal-to-noise ratios. In an alternative embodiment, a substantially high signal-to-noise ratio may be identified. A signal-to-noise ratio may be substantially high when the signal-to-noise ratio is 10. At block 226, a modulation frequency and/or a modulation amplitude corresponding to the maximum or substantially high signal-to-noise ratio may be identified. For example, the identified modulation frequency and the identified modulation amplitude of the determined absorption wavelength range led to generation of respective noise signal and noise-free signal which are used to generate the maximum or substantially high signal-to-noise ratio. At block 228, the identified modulation frequency and the identified modulation amplitude is respectively selected as the optimal modulation frequency and the optimal modulation amplitude corresponding to the determined absorption wavelength range $G_{w1}$. Furthermore, at block 230, a concentration of the individual gas $G_1$ in the gas-mixture may be determined based on the optimal modulation frequency and the optimal modulation amplitude of the determined absorption wavelength range $G_{w1}$ The determination of the concentration of the individual gas based on the optimal modulation frequency and the optimal modulation amplitude is explained in detail with reference to FIG. 4.

Figure 3:
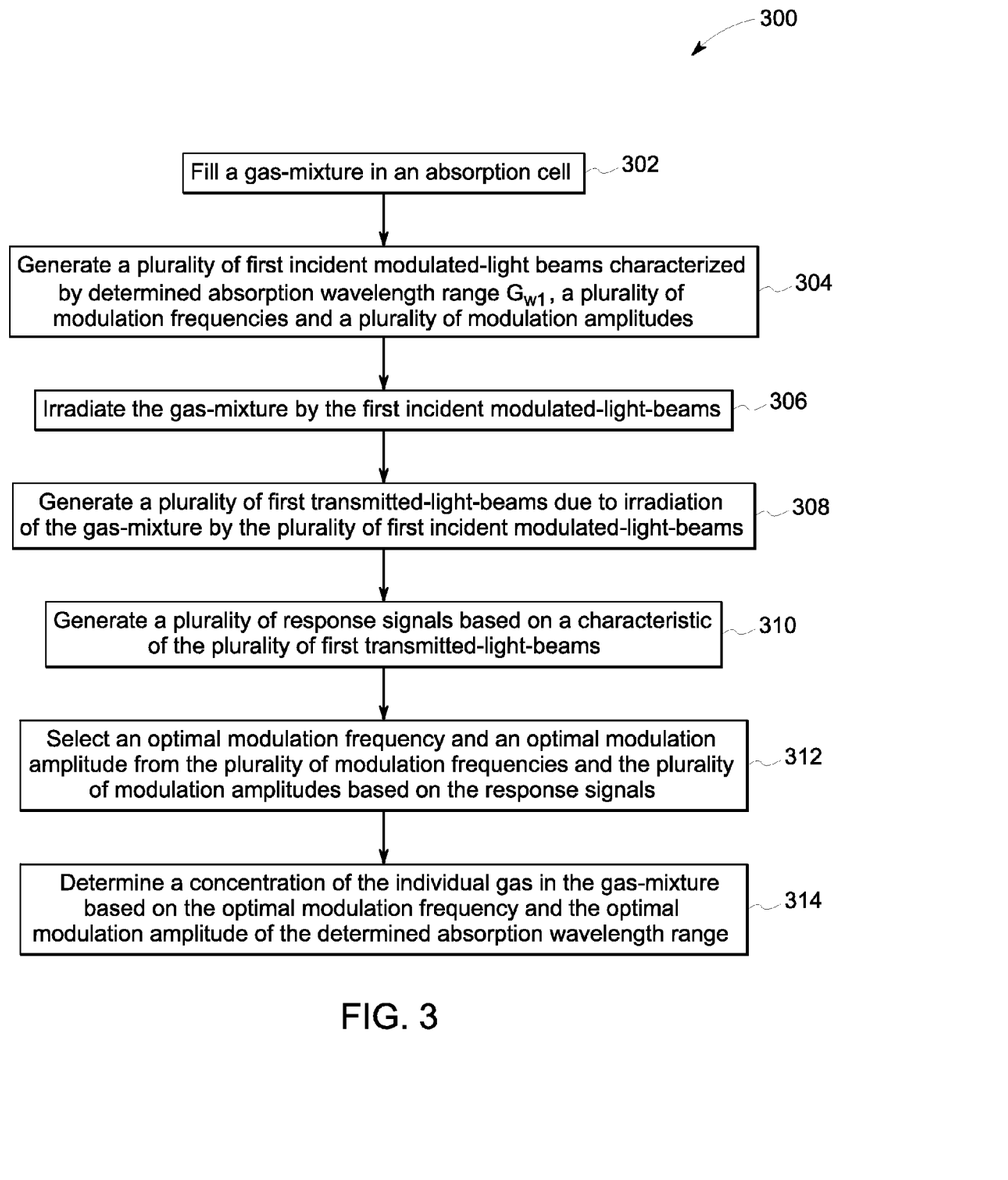
FIG. 3 is a flow chart illustrating a method for analyzing a gas-mixture comprising at least one individual gas $G_1$, in accordance with another embodiment of the present techniques.

FIG. 3 is a flow chart illustrating a method 300 for analyzing a gas-mixture comprising at least one individual gas $G_1$, in accordance with another embodiment of the present techniques. The individual gas $G_1$ corresponds to a determined absorption wavelength range $G_{w1}$ The method 300, for example, may be performed using the system 100 shown in FIG. 1. At block 302, the gas-mixture may be filled in an absorption cell. The absorption cell, for example, may be the absorption cell 110 referred to in FIG. 1. At block 304, a tunable radiation source, such as, the tunable radiation source 106 (see FIG. 1) generates a plurality of first incident modulated-light-beams characterized by determined absorption wavelength range $G_{w1}$, a plurality of modulation frequencies and a plurality of modulation amplitudes. For example, at a time stamp $t_1$, the tunable radiation source generates a first incident modulated-light-beam $IM_1$ characterized by the determined absorption wavelength range $G_{w1}$, a first modulation frequency f1, and a first modulation amplitude a1. Furthermore, at a second time stamp $t_2$, the tunable radiation source generates a first incident modulated-light-beam $IM_2$ characterized by the determined absorption wavelength range $G_{w1}$, the first modulation frequency f1 and a second modulation amplitude a2.

At block 306, the first incident modulated-light-beams irradiate the gas-mixture. At block 308, the irradiation of the first incident modulated light-beams characterized by the determined absorption wavelength range $G_{w1}$, the plurality of the modulation frequencies and the plurality of modulation amplitudes results in absorption of at least a portion of each of the first incident modulated-light-beams by the individual gas resulting in generation of a plurality of first transmitted-light-beams. For example, irradiation of the gas-mixture by the first incident modulated-light-beam $IM_1$, at the time stamp $t_1$, characterized by the determined absorption wavelength range $G_{w1}$, the first modulation frequency f1, and the first modulation amplitude a1 may result in generation of a first transmitted-light-beam $TB_1$. Similarly, the irradiation of the gas-mixture by the first incident modulated-light-beam $IM_2$, at the time stamp $t_2$, characterized by the determined absorption wavelength range $G_{w1}$, the first modulation frequency f1 and a second modulation amplitude a2 may result in generation of a first transmitted-light-beam $TB_2$.

At block 310, a plurality of response signals may be generated based upon the first transmitted-light-beams. In one embodiment, the response signals are representative of intensity of the first transmitted-light-beams. The response signals, for example, may be generated based on a characteristic of the first transmitted-light-beams. The characteristic of the first transmitted-light-beams may include an intensity or power of the first transmitted-light-beams. For example, the response signals may be generated based on the intensity of the first transmitted-light-beams. For example, a response signal $R_1$ may be generated based on an intensity of the first transmitted-light-beam $TB_1$ that is generated due to irradiation of the gas-mixture by the first incident modulated-light-beam $IM_1$ characterized by the determined absorption wavelength range $G_{w1}$, the first modulation frequency f1, and the first modulation amplitude a1. It is noted that the response signal $R_1$ corresponds to the first modulation frequency f1 and the first modulation amplitude a1. Similarly, a response signal $R_2$ may be generated based on an intensity of the first transmitted-light-beam $TB_2$ that is generated due to irradiation of the gas-mixture by the first incident modulated-light-beam $IM_2$ characterized by the determined absorption wavelength range $G_{w1}$, the first modulation frequency f1 and the second modulation amplitude a2. It is noted that the response signal $R_2$ corresponds to the first modulation frequency f1 and the second modulation amplitude a2.

At block 312, an optimal modulation frequency and optimal modulation amplitude may be selected from the plurality of modulation frequencies and the plurality of modulation amplitudes based on the response signals. Particularly, the optimal modulation frequency and the optimal modulation amplitude may be selected from the plurality of modulation frequencies and the plurality of modulation amplitudes based on a signal-to-noise ratio of the response signals. For example, when a response signal R shows maximum signal-to-noise ratio in comparison to rest of the response signals, then a modulation frequency and modulation amplitude that corresponds to the response signal R are selected as the optimal modulation frequency and the optimal modulation amplitude, respectively. For example, if between the response signals $R_1$ and $R_2$, the response signal $R_1$ shows higher signal-to-noise ratio, then the first modulation frequency f1 may be selected as the optimal modulation frequency and the first modulation amplitude a1 may be selected as the optimal modulation amplitude.

Furthermore, at block 314, a concentration of the individual gas in the gas-mixture may be determined based on the optimal modulation frequency and the optimal modulation amplitude of the determined absorption wavelength range $G_{w1}$ The determination of the concentration of the individual gas based on the optimal modulation frequency and the optimal modulation amplitude is explained in detail with reference to FIG. 4.

Figure 4:
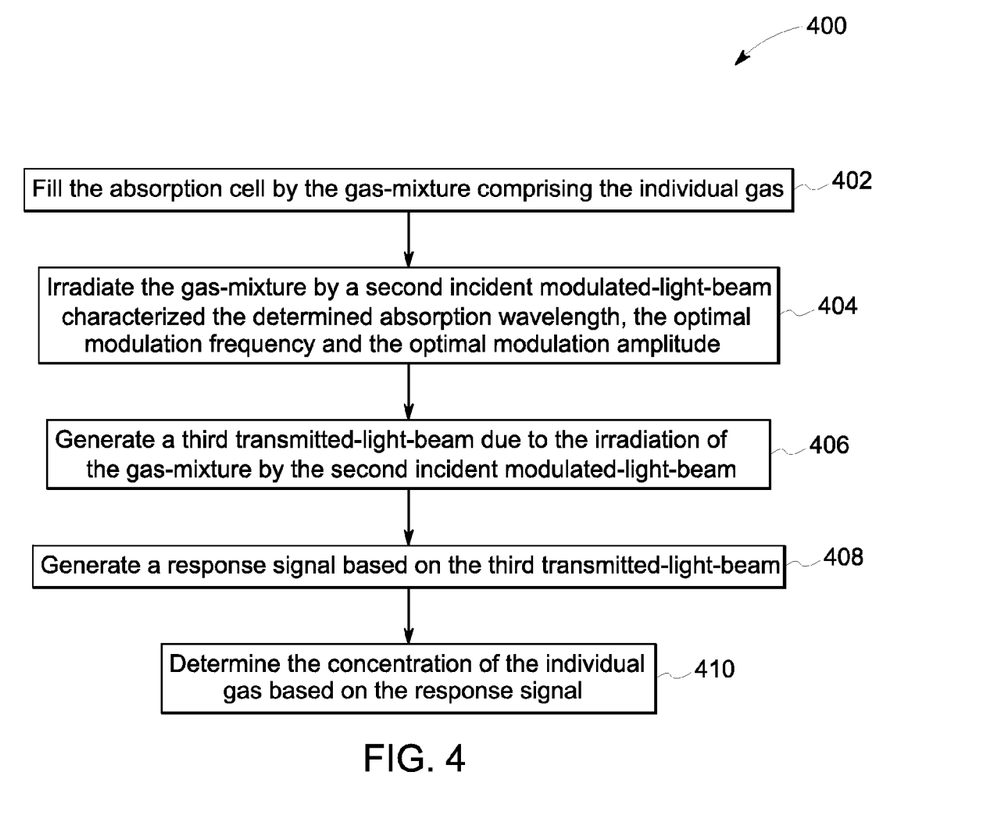
FIG. 4 is a flow chart illustrating a method for determining the concentration of an individual gas in a gas-mixture based on an optimal modulation frequency and an optimal modulation amplitude of the determined absorption wavelength $G_{w1}$ referred to in FIG. 2A and FIG. 2B, in accordance with one embodiment of the present techniques.

FIG. 4 is a flow chart illustrating a method 400 for determining the concentration of an individual gas in a gas-mixture based on an optimal modulation frequency and an optimal modulation amplitude of the determined absorption wavelength $G_{w1}$ referred to in FIG. 2A and FIG. 2B, in accordance with one embodiment of the present techniques. In one embodiment, the method 400 describes block 214 of FIG. 2A in greater detail. In another embodiment, the method 400 describes block 314 of FIG. 3 in greater detail. The gas-mixture, for example, may be the gas-mixture 102 referred to in FIG. 1. Furthermore, the individual gas corresponds to the determined absorption wavelength $G_{w1}$ referred to in FIG. 1-FIG. 3. The optimal modulation frequency and the optimal modulation amplitude may be selected at the block 212 of FIG. 2A and block 312 of FIG. 3.

At block 402, an absorption cell may be filled by the gas-mixture comprising the individual gas that corresponds to the determined absorption wavelength range $G_{w1}$. The absorption cell may be the absorption cell 110 referred to in FIG. 1. At block 404, irradiate the gas-mixture by a second incident modulated-light-beam characterized by the determined absorption wavelength range $G_{w1}$, the optimal modulation frequency and the optimal modulation amplitude. The optimal modulation frequency and the optimal modulation amplitude, for example is selected at block 212 of FIG. 2A or block 312 of FIG. 3. At block 406, irradiation of the gas-mixture by the second incident modulated-light-beam results in generation of a third transmitted-light-beam. At block 408, a response signal may be generated based on the third transmitted-light-beam. The response signal, for example is representative of a characteristic of the third transmitted-light-beam. The response signal, for example, may be generated based on a characteristic of the third transmitted-light-beam. For example, the response signal may be generated based on an intensity and/or energy of the third transmitted-light-beam. The response signal may be a second harmonic signal (the amplitude of intensity at the second harmonic of the optimal modulation frequency) of the third transmitted-light-beams.

At block 410, the concentration of the individual gas may be determined at least based on the response signal. The concentration of the individual gas may be determined by applying Beer-Lambert law on the response signal representative of the intensity of the third transmitted-light-beam and the intensity of the second incident modulated-light-beam.

Figure 5:
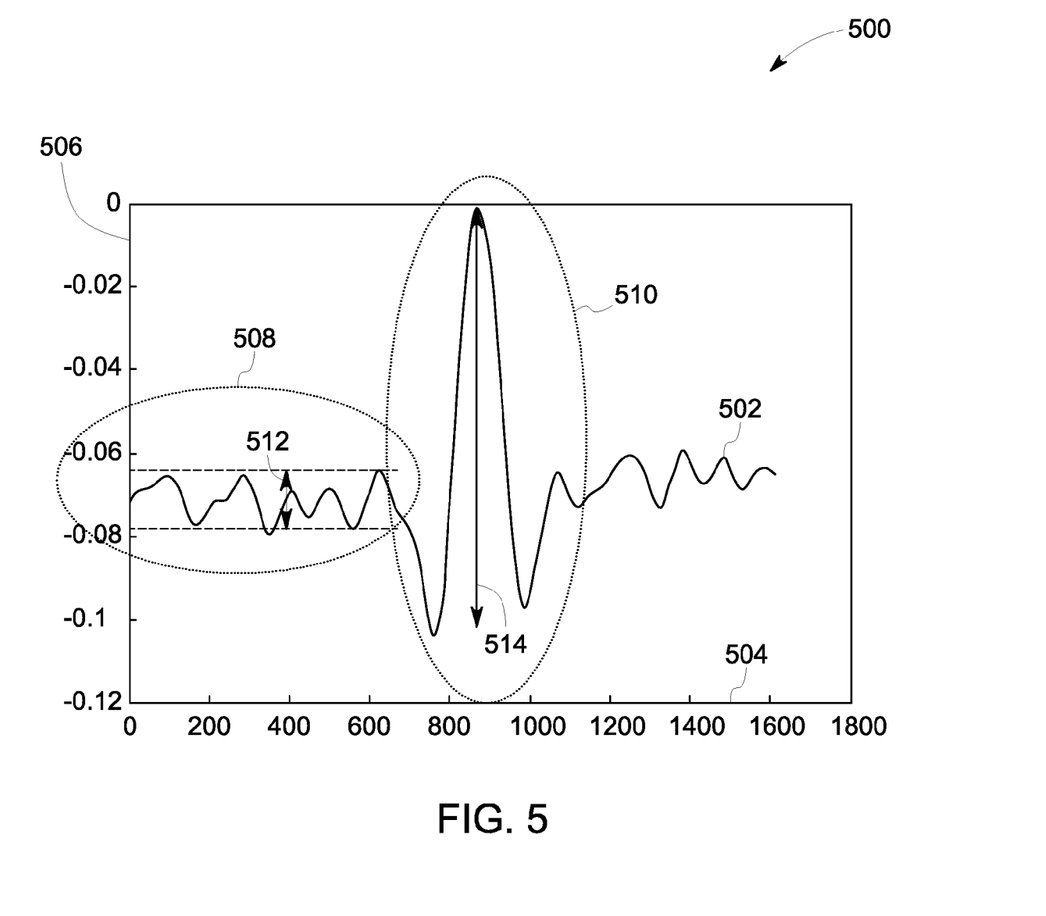
FIG. 5 shows a plot of an experimental response signal to show determination of a signal-to noise-ratio.

FIG. 5 shows a plot 500 of an experimental response signal 502 to show determination of a signal-to noise-ratio. The response signal 502, for example is similar to the response signals generated at block 310 of FIG. 3. The response signal 502 is a second harmonic signal (2 f). The response signal 502 is generated by irradiating a gas-mixture by a first an incident modulated-light beams characterized by an absorption wavelength of 3356 nanometers, a modulation frequency of 1830 Hz, and a modulation depth of 0.028V (0.034 cm−1). Similarly, other response signals may be generated by irradiating the gas-mixture by the absorption wavelength of 3356 nanometers, other modulation frequencies and other modulation amplitudes. X-axis 504 of the plot 500 represents samples and Y-axis 506 represents amplitude of the second harmonic signal 502. A portion 508 of the response signal 502 represents noise and another portion 510 represents signal in the response signal 502. A signal-to-noise ratio $SNR_1$ of the response signal 502, for example may be determined by dividing amplitude 514 of a signal peak in the signal portion 502 by amplitude 512 of a noise peak in the noise portion 508. In the presently contemplated configuration, $SNR_1$ corresponds to the by an absorption wavelength of about 3356 nanometers, the modulation frequency of 1830 Hz, and the modulation depth of 0.028V (0.034 cm−1). Similarly, signal-to-noise ratios corresponding to the absorption wavelength of about 3356 nanometers, other modulation frequencies and other modulation amplitudes may be determined Subsequently modulation amplitude and a modulation frequency that corresponds to a maximum or substantially high signal-to-noise ratio may be chosen as optimal modulation amplitude and an optimal modulation frequency, respectively.

While only certain features of the present systems and methods have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for determining a concentration of at least one individual gas present in a gas-mixture, comprising:
    irradiating a first component, comprising substantially zero concentration of the at least one individual gas, by a plurality of first incident modulated-light-beams characterized by a determined absorption wavelength range, a plurality of modulation frequencies and a plurality of modulation amplitudes to generate a plurality of first transmitted-light-beams, wherein the plurality of first transmitted-light-beams is generated due to substantial failure of absorption of photons of the plurality of first incident modulated-light-beams by the first component;
    irradiating a second component, comprising a determined concentration of the at least one individual gas, by the plurality of first incident modulated-light-beams to generate a plurality of second transmitted-light-beams, wherein the plurality of second transmitted-light-beams is generated due to substantial absorption of the photons of the plurality of first incident modulated-light-beams by the at least one individual gas present in the second component;
    generating a plurality of noise signals comprising at least one of etalon noise and electronic noise, representative of a characteristic of the plurality of first transmitted-light-beams;
    generating a plurality of noise-free signals representative of a characteristic of the plurality of second transmitted-light-beams;
    determining a plurality of signal-to-noise ratios based on the plurality of noise signals and the plurality of noise-free signals;
    selecting a maximum signal-to-noise ratio from the plurality of signal-to-noise ratios;
    selecting an optimal modulation frequency and an optimal modulation amplitude corresponding to the maximum signal-to-noise ratio, from the plurality of modulation frequencies and the plurality of modulation amplitudes based on the plurality of noise signals and the plurality of noise-free signals; and
    determining a concentration of the at least one individual gas in the gas-mixture based on the optimal modulation frequency and the optimal modulation amplitude of the determined absorption wavelength range,
    wherein the determined absorption wavelength range corresponds to the at least one individual gas in the gas-mixture.

2. The method of claim 1, wherein determining the plurality of signal-to-noise ratios comprises dividing amplitudes of the plurality of noise-free signals by corresponding amplitudes of the noise signals.

3. The method of claim 1, wherein the characteristic of the plurality of first transmitted-light-beams comprises intensity or energy of the plurality of first transmitted-light-beams, and the characteristic of the plurality of second transmitted-light-beams comprises intensity or energy of the plurality of second transmitted-light-beams.

4. The method of claim 1, wherein determining the concentration of the at least one individual gas comprises:
    irradiating the gas-mixture by a second incident modulated-light-beam characterized by the determined absorption wavelength range, the optimal modulation frequency and the optimal modulation amplitude, wherein the at least one individual gas absorbs photons of the second incident modulated-light-beam resulting in generation of a third transmitted-light-beam;
    generating a response signal based on the third transmitted-light-beam; and
    determining the concentration of the at least one individual gas at least based on the response signal representative of a characteristic of the third transmitted-light-beam.

5. The method of claim 4, wherein the characteristic of the third transmitted-light-beam comprises one or more of energy and intensity of the third transmitted-light-beam.

6. A system for determining a concentration of at least one individual gas present in a gas-mixture, comprising:
    a first tunable radiation source that:
        generates and directs a plurality of first incident modulated-light-beams to irradiate a first component comprising substantially zero concentration of the at least one individual gas to generate a plurality of first transmitted-light-beams, wherein the plurality of first incident modulated-light-beams are characterized by a determined absorption wavelength range, a plurality of modulation frequencies and a plurality of modulation amplitudes, wherein the plurality of first transmitted-light-beams is generated due to substantial failure of absorption of photons of the plurality of first incident modulated-light-beams by the first component;

generates and directs the plurality of first incident modulated-light-beams to irradiate a second component comprising a determined concentration of the at least one individual gas to generate a plurality of second transmitted-light-beams, wherein the plurality of second transmitted-light-beams is generated due to substantial absorption of the photons of the plurality of first incident modulated-light-beams by the at least one individual gas present in the second component;

a first detector that generates a plurality of noise signals comprising at least one of etalon noise and electronic noise based on the plurality of first transmitted-light-beams, and a plurality of noise-free signals based on the plurality of second transmitted-light-beams;

a processing subsystem that determines a plurality of signal-to-noise ratios based on the plurality of noise signals and the plurality of noise-free signals, selects a maximum signal-to-noise ratio from the plurality of signal-to-noise ratios, selects an optimal modulation frequency and an optimal modulation amplitude corresponding to the maximum signal-to-noise ratio from the plurality of modulation frequencies and the plurality of modulation amplitudes based on the plurality of noise signals and the plurality of noise-free signals;

a subsystem that determines a concentration of the at least one individual gas in the gas-mixture based on the optimal modulation frequency and the optimal modulation amplitude of the determined absorption wavelength range, wherein the determined absorption wavelength range corresponds to the at least one individual gas in the gas-mixture.

7. The system of claim 6, wherein the first component comprises vacuum, a fluid, a gas or a gas-mixture comprising gases that substantially fails to absorb the photons of the plurality of first incident modulated-light-beams characterized by the determined absorption wavelength range and wherein the second component comprises a fluid, a gas or a gas-mixture comprising the at least one individual gas that substantially absorbs the plurality of first incident modulated-light-beams.

8. The system of claim 6, wherein the subsystem comprises:
the absorption cell filled-with the gas-mixture comprising the at least one individual gas;
the tunable radiation source that generates and directs a second incident modulated-light-beam characterized by the determined absorption wavelength range, the optimal modulation frequency and the optimal modulation amplitude to irradiate the gas-mixture resulting in generation of a third transmitted-light-beam;
the processing subsystem that determines the concentration of the at least one individual gas at least based on a response signal representative of a characteristic of the third transmitted-light-beam.

9. The system of claim 8, further comprising the detector that generates the response signal representative of the characteristic of the third transmitted-light-beam.

10. The system of claim 6, wherein the characteristic of the third transmitted-light-beam comprises at least one of intensity and energy content of the third transmitted-light-beam.

11. The method of claim 1, wherein the first component comprises vacuum, a fluid, a gas or a gas-mixture comprising gases that substantially fails to absorb the photons of the plurality of first incident modulated-light-beams characterized by the determined absorption wavelength range and wherein the second component comprises a fluid, a gas or a gas-mixture comprising the at least one individual gas that substantially absorbs the plurality of first incident modulated-light-beams.

* * * * *